(12) United States Patent
Ralph et al.

(10) Patent No.: US 7,713,302 B2
(45) Date of Patent: ***May 11, 2010

(54) INTERVERTEBRAL SPACER DEVICE UTILIZING A SPIRALLY SLOTTED BELLEVILLE WASHER HAVING RADIALLY SPACED CONCENTRIC GROOVES

(75) Inventors: James D. Ralph, Seaside Park, NJ (US); Stephen Tatar, Montville, NJ (US)

(73) Assignee: SpineCore, Inc., Summit, NJ (US)

( * ) Notice: Subject to any disclaimer, the term of this patent is extended or adjusted under 35 U.S.C. 154(b) by 1086 days.

This patent is subject to a terminal disclaimer.

(21) Appl. No.: 10/833,737

(22) Filed: Apr. 28, 2004

(65) Prior Publication Data

US 2004/0204762 A1 Oct. 14, 2004

Related U.S. Application Data

(63) Continuation of application No. 09/975,471, filed on Oct. 11, 2001, now Pat. No. 6,863,688, which is a continuation-in-part of application No. 09/970,479, filed on Oct. 4, 2001, now Pat. No. 6,669,730, which is a continuation-in-part of application No. 09/968,046, filed on Oct. 1, 2001, now abandoned.

(51) Int. Cl.
*A61F 2/44* (2006.01)
(52) U.S. Cl. ............... 623/17.14; 623/17.13; 623/17.15
(58) Field of Classification Search .................. 606/61; 623/17.13–17.15; 411/10, 260, 261, 313, 411/929.2, 943, 247, 531
See application file for complete search history.

(56) References Cited

U.S. PATENT DOCUMENTS

| | | | |
|---|---|---|---|
| 916,421 A | 3/1909 | Crittenden | |
| 1,518,205 A | 12/1924 | Kountz | |
| 2,127,424 A * | 8/1938 | Rolle | ......................... 222/542 |
| 2,193,122 A | 3/1940 | Crabbs | |
| 2,669,896 A | 2/1954 | Clough | |
| 3,867,728 A | 2/1975 | Stubstad | |
| 4,303,001 A | 12/1981 | Trungold | |
| 4,309,777 A | 1/1982 | Patil | |
| 4,605,417 A | 8/1986 | Fleischauer | |
| 4,759,766 A | 7/1988 | Buettner-Janz et al. | |
| 4,759,769 A | 7/1988 | Hedman et al. | |

(Continued)

FOREIGN PATENT DOCUMENTS

DE 3722893 6/1988

(Continued)

*Primary Examiner*—Brian E. Pellegrino
(74) *Attorney, Agent, or Firm*—Lerner, David, Littenberg, Krumholz & Mentlik, LLP

(57) ABSTRACT

An intervertebral spacer device having a pair of opposing plates for seating against opposing vertebral bone surfaces, separated by at least one spring mechanism. The preferred spring mechanism is at least one spirally slotted belleville washer having radially spaced concentric grooves. In a preferred embodiment there is a single such belleville washer which is modified to mount onto a ball-shaped head. The lower plate of this embodiment includes a post extending upwardly from the inner surface of the plate, the post including a ball-shaped head. The modified belleville washer can be rotatably mounted to the head such that the wider portion of the washer seats against the upper plate.

23 Claims, 5 Drawing Sheets

U.S. PATENT DOCUMENTS

| | | |
|---|---|---|
| 4,932,969 A | 6/1990 | Frey et al. |
| 4,955,908 A | 9/1990 | Frey et al. |
| 4,969,907 A | 11/1990 | Koch et al. |
| 4,997,432 A | 3/1991 | Keller |
| 5,002,576 A | 3/1991 | Fuhrmann et al. |
| 5,034,254 A | 7/1991 | Cologna et al. |
| 5,112,178 A | 5/1992 | Overhues et al. |
| 5,122,130 A | 6/1992 | Keller |
| 5,192,327 A | 3/1993 | Brantigan |
| 5,236,460 A | 8/1993 | Barber |
| 5,258,031 A | 11/1993 | Salib et al. |
| 5,306,308 A | 4/1994 | Gross et al. |
| 5,314,477 A | 5/1994 | Marnay |
| 5,370,697 A | 12/1994 | Baumgartner |
| 5,401,269 A | 3/1995 | Buttner-Janz et al. |
| 5,405,400 A | 4/1995 | Linscheid et al. |
| 5,425,773 A | 6/1995 | Boyd et al. |
| 5,443,514 A | 8/1995 | Steffee |
| 5,458,641 A | 10/1995 | Ramirez Jimenez et al. |
| 5,458,642 A | 10/1995 | Beer et al. |
| 5,507,816 A | 4/1996 | Bullivant |
| 5,514,180 A | 5/1996 | Heggeness et al. |
| 5,534,029 A | 7/1996 | Shima |
| 5,549,690 A | 8/1996 | Hollister et al. |
| 5,556,431 A | 9/1996 | Buttner-Janz |
| 5,556,432 A | 9/1996 | Kubein-Meesenburg et al. |
| 5,562,736 A | 10/1996 | Ray et al. |
| 5,562,738 A | 10/1996 | Boyd et al. |
| 5,571,109 A | 11/1996 | Bertagnoli |
| 5,593,456 A | 1/1997 | Merlette |
| 5,645,605 A | 7/1997 | Klawitter |
| 5,653,762 A | 8/1997 | Pisharodi |
| 5,674,296 A | 10/1997 | Bryan et al. |
| 5,676,701 A | 10/1997 | Yuan et al. |
| 5,676,702 A | 10/1997 | Ratron |
| 5,683,464 A | 11/1997 | Wagner et al. |
| 5,683,465 A | 11/1997 | Shinn et al. |
| 5,720,751 A | 2/1998 | Jackson |
| 5,755,796 A | 5/1998 | Ibo et al. |
| 5,776,198 A | 7/1998 | Rabbe et al. |
| 5,782,830 A | 7/1998 | Farris |
| 5,782,832 A | 7/1998 | Larsen et al. |
| 5,827,328 A | 10/1998 | Buttermann |
| 5,865,846 A | 2/1999 | Bryan et al. |
| 5,888,223 A | 3/1999 | Bray, Jr. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima |
| 5,916,267 A | 6/1999 | Tienboon et al. |
| 5,926,685 A | 7/1999 | Krebs et al. |
| 5,928,284 A | 7/1999 | Mehdizadeh |
| 5,976,186 A | 11/1999 | Bao et al. |
| 5,989,291 A | 11/1999 | Ralph et al. |
| 5,989,294 A | 11/1999 | Marlow et al. |
| 6,001,130 A | 12/1999 | Bryan et al. |
| 6,019,792 A | 2/2000 | Cauthen |
| 6,039,763 A | 3/2000 | Shelokov |
| 6,051,751 A | 4/2000 | Sioshansi et al. |
| 6,063,088 A | 5/2000 | Winslow |
| 6,063,121 A | 5/2000 | Xavier et al. |
| 6,066,174 A | 5/2000 | Farris |
| 6,066,175 A | 5/2000 | Henderson et al. |
| 6,080,155 A | 6/2000 | Michelson |
| 6,093,205 A | 7/2000 | McLeod et al. |
| 6,093,207 A | 7/2000 | Pisharodi |
| 6,096,080 A | 8/2000 | Nicholson et al. |
| 6,106,557 A | 8/2000 | Robioneck et al. |
| 6,113,602 A | 9/2000 | Sand |
| 6,113,637 A | 9/2000 | Gill et al. |
| 6,113,638 A | 9/2000 | Williams et al. |
| 6,113,639 A | 9/2000 | Ray et al. |
| 6,136,031 A | 10/2000 | Middleton |
| 6,139,550 A | 10/2000 | Michelson |
| 6,146,421 A | 11/2000 | Gordon et al. |
| 6,156,067 A | 12/2000 | Bryan et al. |
| 6,159,215 A | 12/2000 | Urbahns et al. |
| 6,162,252 A | 12/2000 | Kuras et al. |
| 6,174,311 B1 | 1/2001 | Branch et al. |
| 6,179,873 B1 | 1/2001 | Zientek et al. |
| 6,179,874 B1 | 1/2001 | Cauthen |
| 6,190,413 B1 | 2/2001 | Sutcliffe et al. |
| 6,190,414 B1 | 2/2001 | Young et al. |
| 6,193,757 B1 | 2/2001 | Foley et al. |
| 6,214,005 B1 | 4/2001 | Benzel et al. |
| 6,214,049 B1 | 4/2001 | Gayer et al. |
| 6,224,607 B1 | 5/2001 | Michelson |
| 6,228,118 B1 | 5/2001 | Gordon |
| 6,231,609 B1 | 5/2001 | Mehdizadeh |
| 6,235,034 B1 | 5/2001 | Bray |
| 6,235,060 B1 | 5/2001 | Kubein-Meesenburg et al. |
| 6,241,732 B1 | 6/2001 | Overaker et al. |
| 6,241,769 B1 | 6/2001 | Nicholson et al. |
| 6,261,293 B1 | 7/2001 | Nicholson et al. |
| 6,261,296 B1 | 7/2001 | Aebi et al. |
| 6,261,324 B1 | 7/2001 | Merlette |
| 6,277,149 B1 | 8/2001 | Boyle et al. |
| 6,296,647 B1 | 10/2001 | Robioneck et al. |
| 6,296,665 B1 | 10/2001 | Strnad et al. |
| 6,319,257 B1 | 11/2001 | Carignan et al. |
| 6,325,828 B1 | 12/2001 | Dennis et al. |
| 6,342,057 B1 | 1/2002 | Brace et al. |
| 6,348,071 B1 | 2/2002 | Steffee et al. |
| 6,368,350 B1 | 4/2002 | Erickson et al. |
| 6,375,682 B1 | 4/2002 | Fleischmann et al. |
| 6,395,030 B1 | 5/2002 | Songer et al. |
| 6,395,032 B1 | 5/2002 | Gauchet |
| 6,395,035 B2 | 5/2002 | Bresina et al. |
| 6,413,259 B1 | 7/2002 | Lyons et al. |
| 6,416,551 B1 | 7/2002 | Keller |
| 6,428,544 B1 | 8/2002 | Ralph et al. |
| 6,432,106 B1 | 8/2002 | Fraser et al. |
| 6,436,102 B1 | 8/2002 | Ralph et al. |
| 6,440,168 B1 | 8/2002 | Cauthen |
| 6,447,547 B1 | 9/2002 | Michelson |
| 6,461,359 B1 | 10/2002 | Tribus et al. |
| 6,468,310 B1 | 10/2002 | Ralph et al. |
| 6,471,725 B1 | 10/2002 | Ralph et al. |
| 6,478,796 B2 | 11/2002 | Zucherman et al. |
| 6,478,800 B1 | 11/2002 | Fraser et al. |
| 6,478,801 B1 | 11/2002 | Ralph et al. |
| 6,488,710 B2 | 12/2002 | Besselink et al. |
| 6,517,580 B1 | 2/2003 | Ramadan et al. |
| 6,520,996 B1 | 2/2003 | Manasas et al. |
| 6,524,312 B2 | 2/2003 | Landry et al. |
| 6,527,786 B1 | 3/2003 | Davis et al. |
| 6,527,804 B1 | 3/2003 | Gauchet et al. |
| 6,527,806 B2 | 3/2003 | Ralph et al. |
| 6,540,785 B1 | 4/2003 | Gill et al. |
| 6,551,316 B1 | 4/2003 | Rinner et al. |
| 6,554,864 B2 | 4/2003 | Ralph et al. |
| 6,562,047 B2 | 5/2003 | Ralph et al. |
| 6,562,073 B2 | 5/2003 | Foley |
| 6,572,653 B1 | 6/2003 | Simonson |
| 6,576,017 B2 | 6/2003 | Foley et al. |
| 6,579,290 B1 | 6/2003 | Hardcastle et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,582,468 B1 | 6/2003 | Gauchet |
| 6,589,247 B2 | 7/2003 | McGahan et al. |
| 6,592,624 B1 | 7/2003 | Fraser et al. |
| 6,607,558 B2 | 8/2003 | Kuras |
| 6,607,559 B2 | 8/2003 | Ralph et al. |

| | | | | | | |
|---|---|---|---|---|---|---|
| 6,610,092 B2 | 8/2003 | Ralph et al. | | 2002/0111685 A1 | 8/2002 | Ralph et al. |
| 6,610,093 B1 | 8/2003 | Pisharodi | | 2002/0111686 A1 | 8/2002 | Ralph et al. |
| 6,623,525 B2 | 9/2003 | Ralph et al. | | 2002/0111687 A1 | 8/2002 | Ralph et al. |
| 6,641,614 B1 | 11/2003 | Wagner et al. | | 2002/0116009 A1 | 8/2002 | Fraser et al. |
| 6,645,248 B2 | 11/2003 | Casutt | | 2002/0123750 A1 | 9/2002 | Eisermann et al. |
| 6,645,249 B2 | 11/2003 | Ralph et al. | | 2002/0128714 A1 | 9/2002 | Manasas et al. |
| 6,652,525 B1 | 11/2003 | Assaker et al. | | 2002/0128715 A1 | 9/2002 | Bryan et al. |
| 6,652,533 B2 | 11/2003 | O'Neil | | 2002/0143399 A1 | 10/2002 | Sutcliffe |
| 6,666,866 B2 | 12/2003 | Martz et al. | | 2002/0147450 A1 | 10/2002 | LeHuec et al. |
| 6,669,699 B2 | 12/2003 | Ralph et al. | | 2002/0161375 A1 | 10/2002 | Ralph et al. |
| 6,669,730 B2 | 12/2003 | Ralph et al. | | 2002/0169508 A1 | 11/2002 | Songer et al. |
| 6,669,731 B2 | 12/2003 | Ralph et al. | | 2002/0177897 A1 | 11/2002 | Michelson |
| 6,669,732 B2 | 12/2003 | Serhan et al. | | 2002/0188295 A1 | 12/2002 | Martz et al. |
| 6,673,113 B2 | 1/2004 | Ralph et al. | | 2002/0193880 A1 | 12/2002 | Fraser |
| 6,679,887 B2 | 1/2004 | Nicholson et al. | | 2003/0009223 A1 | 1/2003 | Fehling et al. |
| 6,679,915 B1 | 1/2004 | Cauthen | | 2003/0009224 A1 | 1/2003 | Kuras |
| 6,682,562 B2 | 1/2004 | Viart et al. | | 2003/0014057 A1 | 1/2003 | Ralph et al. |
| 6,692,495 B1 | 2/2004 | Zacouto | | 2003/0014109 A1 | 1/2003 | Ralph et al. |
| 6,706,068 B2 | 3/2004 | Ferree | | 2003/0014110 A1 | 1/2003 | Ralph et al. |
| 6,709,439 B2 | 3/2004 | Rogers et al. | | 2003/0014111 A1 | 1/2003 | Ralph et al. |
| 6,712,825 B2 | 3/2004 | Aebi et al. | | 2003/0014112 A1 | 1/2003 | Ralph et al. |
| 6,716,245 B2 | 4/2004 | Pasquet et al. | | 2003/0014113 A1 | 1/2003 | Ralph et al. |
| 6,755,841 B2 | 6/2004 | Fraser et al. | | 2003/0014114 A1 | 1/2003 | Ralph et al. |
| 6,764,515 B2 | 7/2004 | Ralph et al. | | 2003/0014115 A1 | 1/2003 | Ralph et al. |
| 6,793,678 B2 | 9/2004 | Hawkins | | 2003/0014116 A1 | 1/2003 | Ralph et al. |
| 6,800,093 B2 | 10/2004 | Nicholson et al. | | 2003/0023245 A1 | 1/2003 | Ralph et al. |
| 6,827,743 B2 | 12/2004 | Eisermann et al. | | 2003/0023309 A1 | 1/2003 | Ralph et al. |
| 6,835,206 B2 | 12/2004 | Jackson | | 2003/0023310 A1 | 1/2003 | Ralph et al. |
| 6,837,905 B1 | 1/2005 | Lieberman | | 2003/0028197 A1 | 2/2003 | Hanson et al. |
| 6,863,688 B2 | 3/2005 | Ralph et al. | | 2003/0028249 A1 | 2/2003 | Baccelli et al. |
| 6,875,213 B2 | 4/2005 | Michelson | | 2003/0028252 A1 | 2/2003 | Ralph et al. |
| 6,908,484 B2 | 6/2005 | Zubok et al. | | 2003/0040796 A1 | 2/2003 | Ferree |
| 6,918,934 B2 | 7/2005 | Ralph et al. | | 2003/0040801 A1 | 2/2003 | Ralph et al. |
| 6,923,814 B1 | 8/2005 | Hildebrand et al. | | 2003/0045939 A1 | 3/2003 | Casutt |
| 6,981,990 B2 | 1/2006 | Keller et al. | | 2003/0055503 A1 | 3/2003 | O'Neil |
| 6,991,654 B2 | 1/2006 | Foley | | 2003/0060886 A1 | 3/2003 | Van Hoeck et al. |
| 7,022,139 B2 | 4/2006 | Errico et al. | | 2003/0065395 A1 | 4/2003 | Ralph et al. |
| 7,063,725 B2 | 6/2006 | Foley | | 2003/0069586 A1 | 4/2003 | Errico et al. |
| 7,070,598 B2 | 7/2006 | Lim et al. | | 2003/0069642 A1 | 4/2003 | Ralph et al. |
| 7,087,055 B2 | 8/2006 | Lim et al. | | 2003/0074064 A1 | 4/2003 | Gerbec et al. |
| 7,115,132 B2 | 10/2006 | Errico et al. | | 2003/0074067 A1 | 4/2003 | Errico et al. |
| 7,118,579 B2 | 10/2006 | Michelson | | 2003/0078662 A1 | 4/2003 | Ralph et al. |
| 7,118,580 B1 | 10/2006 | Beyersdorff et al. | | 2003/0078663 A1 | 4/2003 | Ralph et al. |
| 7,125,425 B2 | 10/2006 | Foley et al. | | 2003/0078664 A1 | 4/2003 | Ralph et al. |
| 7,223,291 B2 | 5/2007 | Errico et al. | | 2003/0078665 A1 | 4/2003 | Ralph et al. |
| 7,238,203 B2 | 7/2007 | Bagga et al. | | 2003/0078666 A1 | 4/2003 | Ralph et al. |
| 7,270,680 B2 * | 9/2007 | Ralph et al. ............. 623/17.14 | | 2003/0078667 A1 | 4/2003 | Manasas et al. |
| 2001/0005796 A1 | 6/2001 | Zdeblick et al. | | 2003/0078668 A1 | 4/2003 | Michelson |
| 2001/0007073 A1 | 7/2001 | Zucherman et al. | | 2003/0083747 A1 | 5/2003 | Winterbottom et al. |
| 2001/0010001 A1 | 7/2001 | Michelson | | 2003/0083749 A1 | 5/2003 | Kuslich et al. |
| 2001/0012938 A1 | 8/2001 | Zucherman et al. | | 2003/0093153 A1 | 5/2003 | Banick et al. |
| 2001/0016773 A1 | 8/2001 | Serhan et al. | | 2003/0100949 A1 | 5/2003 | Michelson |
| 2001/0016774 A1 | 8/2001 | Bresina et al. | | 2003/0100951 A1 | 5/2003 | Serhan et al. |
| 2001/0020170 A1 | 9/2001 | Zucherman et al. | | 2003/0109928 A1 | 6/2003 | Pasquet et al. |
| 2001/0027343 A1 | 10/2001 | Keller | | 2003/0120344 A1 | 6/2003 | Michelson |
| 2001/0039452 A1 | 11/2001 | Zucherman et al. | | 2003/0125739 A1 | 7/2003 | Bagga et al. |
| 2002/0017789 A1 | 2/2002 | Holmes et al. | | 2003/0125748 A1 | 7/2003 | Li et al. |
| 2002/0035400 A1 | 3/2002 | Bryan et al. | | 2003/0135278 A1 | 7/2003 | Eckman |
| 2002/0045901 A1 | 4/2002 | Wagner et al. | | 2003/0135279 A1 | 7/2003 | Michelson |
| 2002/0045904 A1 | 4/2002 | Fuss et al. | | 2003/0149438 A1 | 8/2003 | Nichols et al. |
| 2002/0062131 A1 | 5/2002 | Gallo | | 2003/0149482 A1 | 8/2003 | Michelson |
| 2002/0082597 A1 | 6/2002 | Fraser | | 2003/0167091 A1 | 9/2003 | Scharf |
| 2002/0082695 A1 | 6/2002 | Neumann | | 2003/0167092 A1 | 9/2003 | Foley |
| 2002/0082701 A1 | 6/2002 | Zdeblick et al. | | 2003/0171813 A1 | 9/2003 | Kiester |
| 2002/0084562 A1 | 7/2002 | Kelsey | | 2003/0176921 A1 | 9/2003 | Lawson |
| 2002/0099377 A1 | 7/2002 | Zucherman et al. | | 2003/0176922 A1 | 9/2003 | Lawson et al. |
| 2002/0107571 A1 | 8/2002 | Foley | | 2003/0176923 A1 | 9/2003 | Keller et al. |
| 2002/0107572 A1 | 8/2002 | Foley et al. | | 2003/0181982 A1 | 9/2003 | Kuslich |
| 2002/0111679 A1 | 8/2002 | Zucherman et al. | | 2003/0187453 A1 | 10/2003 | Schlapfer et al. |
| 2002/0111681 A1 | 8/2002 | Ralph et al. | | 2003/0187454 A1 | 10/2003 | Gill et al. |
| 2002/0111682 A1 | 8/2002 | Ralph et al. | | 2003/0187508 A1 | 10/2003 | Cauthen |
| 2002/0111683 A1 | 8/2002 | Ralph et al. | | 2003/0191534 A1 | 10/2003 | Viart et al. |
| 2002/0111684 A1 | 8/2002 | Ralph et al. | | 2003/0195632 A1 | 10/2003 | Foley et al. |

| | | |
|---|---|---|
| 2003/0199981 A1 | 10/2003 | Ferree |
| 2003/0199983 A1 | 10/2003 | Michelson |
| 2003/0204260 A1 | 10/2003 | Ferree |
| 2003/0208271 A1 | 11/2003 | Kuras |
| 2003/0208274 A1 | 11/2003 | Davis |
| 2003/0216744 A1 | 11/2003 | Longhini et al. |
| 2003/0216810 A1 | 11/2003 | Ralph et al. |
| 2003/0220690 A1 | 11/2003 | Cauthen |
| 2003/0220694 A1 | 11/2003 | Cauthen |
| 2003/0225408 A1 | 12/2003 | Nichols et al. |
| 2003/0225416 A1 | 12/2003 | Bonvallet et al. |
| 2003/0229358 A1 | 12/2003 | Errico et al. |
| 2003/0229397 A1 | 12/2003 | Davis |
| 2003/0233097 A1 | 12/2003 | Ferree |
| 2003/0233145 A1 | 12/2003 | Landry et al. |
| 2003/0233148 A1 | 12/2003 | Ferree |
| 2003/0236520 A1 | 12/2003 | Lim et al. |
| 2004/0002758 A1 | 1/2004 | Landry et al. |
| 2004/0002759 A1 | 1/2004 | Ferree |
| 2004/0002761 A1 | 1/2004 | Rogers et al. |
| 2004/0002762 A1 | 1/2004 | Hawkins |
| 2004/0006343 A1 | 1/2004 | Sevrain |
| 2004/0010254 A1 | 1/2004 | Cook et al. |
| 2004/0010316 A1 | 1/2004 | William et al. |
| 2004/0021042 A1 | 2/2004 | Stephen et al. |
| 2004/0024406 A1 | 2/2004 | Ralph et al. |
| 2004/0024407 A1 | 2/2004 | Ralph et al. |
| 2004/0024459 A1 | 2/2004 | Ferree |
| 2004/0024461 A1 | 2/2004 | Ferree |
| 2004/0024462 A1 | 2/2004 | Ferree et al. |
| 2004/0030387 A1 | 2/2004 | Landry et al. |
| 2004/0030389 A1 | 2/2004 | Ferree |
| 2004/0030390 A1 | 2/2004 | Ferree |
| 2004/0030391 A1 | 2/2004 | Ferree |
| 2004/0034426 A1 | 2/2004 | Errico et al. |
| 2004/0068318 A1 | 4/2004 | Coates et al. |
| 2004/0068320 A1 | 4/2004 | Robie et al. |
| 2004/0078079 A1 | 4/2004 | Foley |
| 2004/0106927 A1 | 6/2004 | Ruffner et al. |
| 2004/0117022 A1 | 6/2004 | Marnay et al. |
| 2004/0133281 A1 | 7/2004 | Khandkar et al. |
| 2004/0138750 A1 | 7/2004 | Mitchell |
| 2004/0143332 A1 | 7/2004 | Krueger et al. |
| 2004/0148028 A1 | 7/2004 | Ferree et al. |
| 2004/0167535 A1 | 8/2004 | Errico et al. |
| 2004/0167628 A1 | 8/2004 | Foley |
| 2004/0215198 A1 | 10/2004 | Marnay et al. |
| 2004/0220567 A1 | 11/2004 | Eisermann et al. |
| 2004/0220582 A1 | 11/2004 | Keller |
| 2004/0243240 A1 | 12/2004 | Beaurain et al. |
| 2004/0267369 A1 | 12/2004 | Lyons et al. |
| 2005/0043803 A1 | 2/2005 | Schultz et al. |
| 2005/0119665 A1 | 6/2005 | Keller |
| 2005/0159819 A1 | 7/2005 | McCormack et al. |
| 2005/0182416 A1 | 8/2005 | Lim et al. |
| 2005/0256577 A1 | 11/2005 | Baumgartner et al. |
| 2005/0283237 A1 | 12/2005 | Zucherman et al. |
| 2006/0064107 A1 | 3/2006 | Bertagnoli et al. |
| 2006/0074432 A1 | 4/2006 | Stad et al. |
| 2006/0241643 A1 | 10/2006 | Lim et al. |
| 2007/0106388 A1 | 5/2007 | Michelson |
| 2007/0123907 A1 | 5/2007 | Weber |
| 2007/0161991 A1 | 7/2007 | Altarac et al. |
| 2007/0260315 A1 | 11/2007 | Foley et al. |

FOREIGN PATENT DOCUMENTS

| | | |
|---|---|---|
| DE | 43 15 757 | 11/1994 |
| DE | 199 03 763 | 8/2000 |
| DE | 10130825 | 3/2002 |
| EP | 0 392 076 A1 | 10/1990 |
| EP | 0 599 419 A2 | 6/1994 |
| EP | 599419 | 6/1994 |
| EP | 1 222 903 A1 | 7/2002 |
| EP | 1219266 | 7/2002 |
| FR | 2 718 635 A1 | 10/1995 |
| FR | 2 730 159 A1 | 8/1996 |
| FR | 2 805 985 A1 | 9/2001 |
| FR | 2 824 261 A1 | 11/2001 |
| RU | 2 077 288 C1 | 4/1997 |
| SU | 1560184 | 4/1990 |
| WO | WO-91/13598 | 9/1991 |
| WO | WO-94/04100 A1 | 3/1994 |
| WO | WO-97/10776 A1 | 3/1997 |
| WO | WO-01/01893 | 1/2001 |
| WO | WO-01/62191 A2 | 8/2001 |
| WO | WO-01/93785 | 12/2001 |
| WO | WO-01/93786 A2 | 12/2001 |
| WO | WO-03/084449 A1 | 10/2003 |
| WO | WO-2004/019828 A1 | 3/2004 |
| WO | WO-2004/026186 A1 | 4/2004 |

\* cited by examiner

INTERVERTEBRAL SPACER DEVICE UTILIZING A SPIRALLY SLOTTED BELLEVILLE WASHER HAVING RADIALLY SPACED CONCENTRIC GROOVES

CROSS-REFERENCE TO RELATED APPLICATION

This application is a continuation application of U.S. patent application Ser. No. 09/975,471 (filed Oct. 11, 2001) entitled "Intervertebral Spacer Device Utilizing A Spirally Slotted Belleville Washer Having Radially Spaced Concentric Grooves", now U.S. Pat. No. 6,863,688 ("the '688 patent"), which is a continuation-in-part of U.S. patent application Ser. No. 09/970,479 (filed Oct. 1, 2001) entitled "Intervertebral Spacer Device Utilizing A Spirally Slotted Belleville Washer Having Radially Extending Grooves", now U.S. Pat. No. 6,669,730 ("the '730 patent), which is a continuation-in-part of Ser. No. 09/968,046 (filed Oct. 1, 2001) entitled "Intervertebral Spacer Device Utilizing A Belleville Washer Having Radially Extending Grooves", now abandoned. of the above mentioned applications are hereby incorporated by

FIELD OF THE INVENTION

This invention relates generally to a spinal implant assembly for implantation into the intervertebral space between adjacent vertebral bones to simultaneously provide stabilization and continued flexibility and proper anatomical motion, and more specifically to such a device which utilizes a spirally slotted belleville washer, having radially spaced concentric grooves, as a restoring force generating element.

BACKGROUND OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the present invention to provide a new and novel intervertebral spacer which stabilizes the spine without promoting a bone fusion across the intervertebral space.

It is further an object of the present invention to provide an implant device which stabilizes the spine while still permitting normal motion.

It is further an object of the present invention to provide a device for implantation into the intervertebral space which does not promote the abnormal distribution of biomechanical stresses on the patient's spine.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flexible intervertebral spacer device comprising a pair of spaced apart base plates, arranged in a substantially parallel planar alignment (or slightly offset relative to one another in accordance with proper lordotic angulation) and coupled to one another by means of a spring mechanism. In particular, this spring mechanism provides a strong restoring force when a compressive load is applied to the plates, and may also permit rotation of the two plates relative to one another. While there are a wide variety of embodiments contemplated, a preferred embodiment includes a belleville washer utilized as the restoring force providing element, the belleville washer being spirally slotted and having radially spaced concentric grooves.

More particularly, as the assembly is to be positioned between the facing surfaces of adjacent vertebral bodies, the base plates should have substantially flat external surfaces which seat against the opposing bone surfaces. Inasmuch as these bone surfaces are often concave, it is anticipated that the opposing plates may be convex in accordance with the average topology of the spinal anatomy. In addition, the plates are to mate with the bone surfaces in such a way as to not rotate relative thereto. (The plates rotate relative to one another, but not with respect to the bone surfaces to which they are each in contact with.) In order to prevent rotation of a plate relative to the bone, the upper and lower plates can include a porous coating into which the bone of the vertebral body can grow. (Note that this limited fusion of the bone to the base plate does not extend across the intervertebral space.)

In some embodiments (not in the preferred embodiment), between the base plates, on the exterior of the device, there is included a circumferential wall which is resilient and which simply prevents vessels and tissues from entering within the interior of the device. This resilient wall may comprise a porous fabric or a semi-impermeable elastomeric material. Suitable tissue compatible materials meeting the simple mechanical requirements of flexibility and durability are prevalent in a number of medical fields including cardiovascular medicine, wherein such materials are utilized for venous and arterial wall repair, or for use with artificial valve replacements. Alternatively, suitable plastic materials are utilized in the surgical repair of gross damage to muscles and organs. Still further materials that could be utilized herein may be found in the field of orthopedic in conjunction with ligament and tendon repair. It is anticipated that future developments in this area will produce materials that are compatible for use with this invention, the breadth of which shall not be limited by the choice of such a material.

As introduced above, the internal structure of the present invention comprises a spring member, which provides a restoring force when compressed. More particularly, it is desirable that the restoring forces be directed outward against the opposing plates, when a compressive load is applied to the plates. In addition, in certain embodiments, it is necessary that the restoring force providing subassembly not substantially interfere with the rotation of the opposing plates relative to one another. In the preferred embodiment, the spring subassembly is configured to allow rotation of the plates relative to one another. In other embodiments, the spring subassembly can be configured to either allow rotation of the plates, or prevent rotation of the plates (through the tightening of a set screw as discussed below). As further mentioned above, the force restoring member comprises at least one belleville washer.

Belleville washers are washers which are generally bowed in the radial direction. Specifically, they have a radial convexity (i.e., the height of the washer is not linearly related to the radial distance, but may, for example, be parabolic in shape). The restoring force of a belleville washer is proportional to the elastic properties of the material. In addition, the magnitude of the compressive load support and the restoring force provided by the belleville washer may be modified by providing slots and/or grooves in the washer. In the preferred embodiment of the present invention, the belleville washer utilized as the force restoring member is spirally slotted, with the slots initiating on the periphery of the washer and extending along arcs which are generally radially inwardly directed a distance toward the center of the bowed disc, and has radially uniformly spaced concentric grooves of uniform width and depth.

As a compressive load is applied to a belleville washer, the forces are directed into a hoop stress which tends to radially expand the washer. This hoop stress is counterbalanced by the material strength of the washer, and the strain of the material causes a deflection in the height of the washer. Stated equivalently, a belleville washer responds to a compressive load by deflecting compressively, but provides a restoring force which is proportional to the elastic modulus of the material in a hoop stressed condition. With slots and/or radially spaced concentric grooves formed in the washer, it expands and restores itself far more elastically than a solid washer.

In general, the belleville washer is one of the strongest configurations for a spring, and is highly suitable for use as a restoring force providing subassembly for use in an intervertebral spacer element which must endure considerable cyclical loading in an active human adult.

In the preferred embodiment of the present invention, a single modified belleville washer, which is of the slotted variety and has radially spaced concentric grooves as described above, is utilized in conjunction with a ball-shaped post on which it is free to rotate through a range of angles (thus permitting the plates to rotate relative to one another through a corresponding range of angles). More particularly, this embodiment comprises a pair of spaced apart base plates, one of which is simply a disc shaped member (preferably shaped to match the end of an intervertebral disc) having an external face (having the porous coating discussed above) and an internal face having an annular retaining wall (the purpose of which will be discussed below). The other of the plates is similarly shaped, having an exterior face with a porous coating, but further includes on its internal face a central post portion which rises out of the internal face at a nearly perpendicular angle. The top of this post portion includes a ball-shaped knob. The knob includes a central threaded axial bore which receives a small set screw. Prior to the insertion of the set screw, the ball-shaped head of the post can deflect radially inward (so that the ball-shaped knob contracts). The insertion of the set screw eliminates the capacity for this deflection.

As introduced above, a modified and spirally slotted belleville washer having radially spaced concentric grooves is mounted to this ball-shaped knob in such a way that it may rotate freely through a range of angles equivalent to the fraction of normal human spine rotation (to mimic normal disc rotation). The belleville washer of this design is modified by including an enlarged inner circumferential portion (at the center of the washer) which accommodates the ball-shaped portion of the post. More particularly, the enlarged portion of the modified belleville washer includes a curvate volume having a substantially constant radius of curvature which is also substantially equivalent to the radius of the ball-shaped head of the post. The deflectability of the ball-shaped head of the post, prior to the insertion of the set screw, permits the head to be inserted into the interior volume at the center of the belleville washer. Subsequent introduction of the set screw into the axial bore of the post prevents the ball-shaped head from deflecting. Thereby, the washer can be secured to the ball-shaped head so that it can rotate thereon through a range of proper lordotic angles (in some embodiments, a tightening of the set screw locks the washer on the ball-shaped head at one of the lordotic angles).

This assembly provides ample spring-like performance with respect to axial compressive loads, as well as long cycle life to mimic the axial biomechanical performance of the normal human intervertebral disc. The spiral slots and radially spaced concentric grooves of the belleville washer allow the washer to expand radially as the slots and grooves widen under the load, only to spring back into its undeflected shape upon the unloading of the spring. As the washer compresses and decompresses, the annual retaining wall maintains the wide end of the washer within a prescribed boundary on the internal face of the base plate which it contacts, and an annular retaining ring maintains the wide end of the washer against the internal face.

Finally, inasmuch as the human body has a tendency to produce fibrous tissues in perceived voids, such as may be found within the interior of the present invention, and such fibrous tissues may interfere with the stable and/or predicted functioning of the device, some embodiments of the present invention (although not the preferred embodiment) will be filled with a highly resilient elastomeric material. The material itself should be highly biologically inert, and should not substantially interfere with the restoring forces provided by the spring-like mechanisms therein. Suitable materials may include hydrophilic monomers such as are used in contact lenses. Alternative materials include silicone jellies and collagens such as have been used in cosmetic applications. As with the exterior circumferential wall, which was described above as having a variety of suitable alternative materials, it is anticipated that future research will produce alternatives to the materials described herein, and that the future existence of such materials which may be used in conjunction with the present invention shall not limit the breadth thereof.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
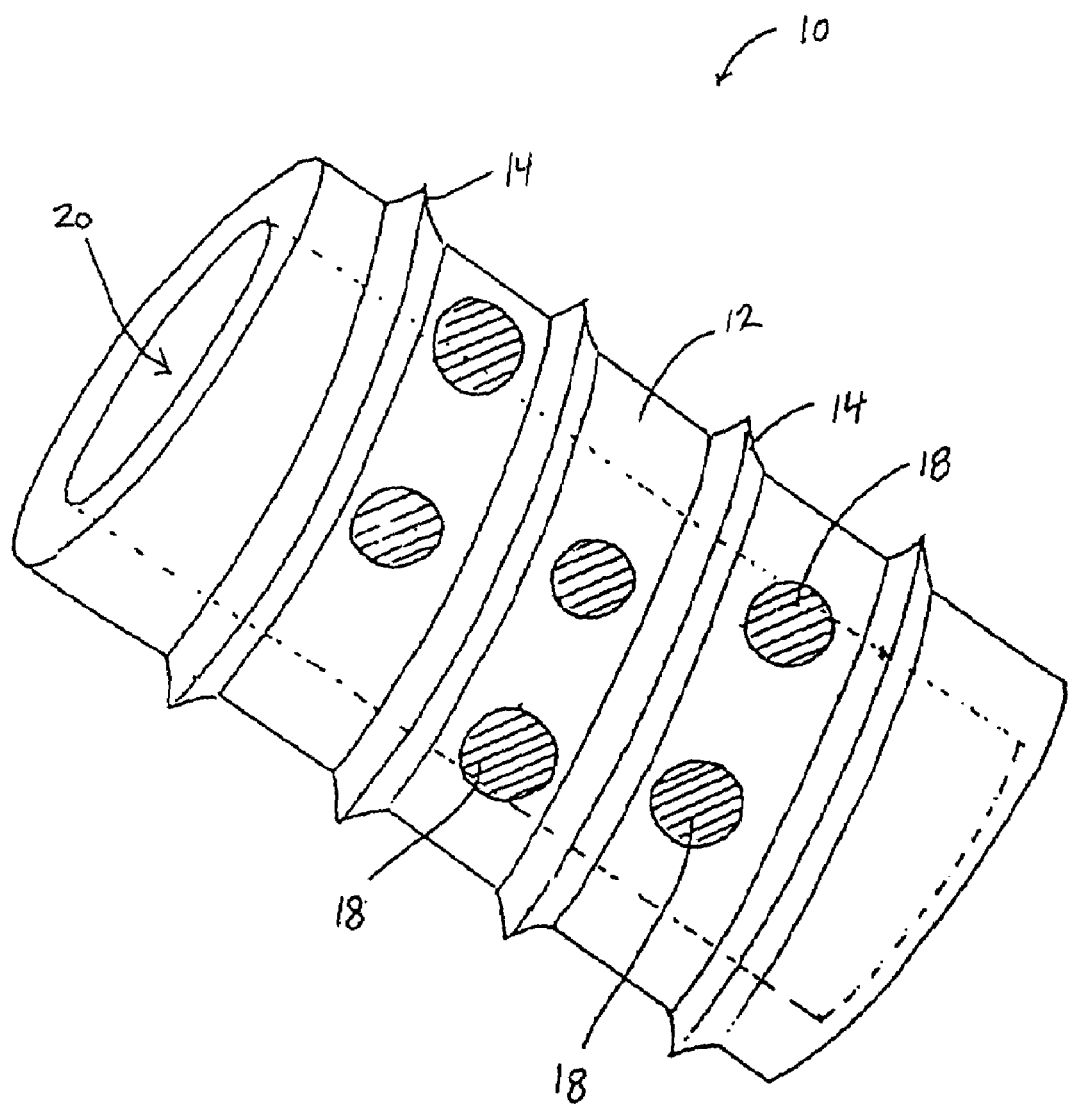
FIG. 1 is a side perspective view of an interbody fusion device of the prior art.
Figure 2:
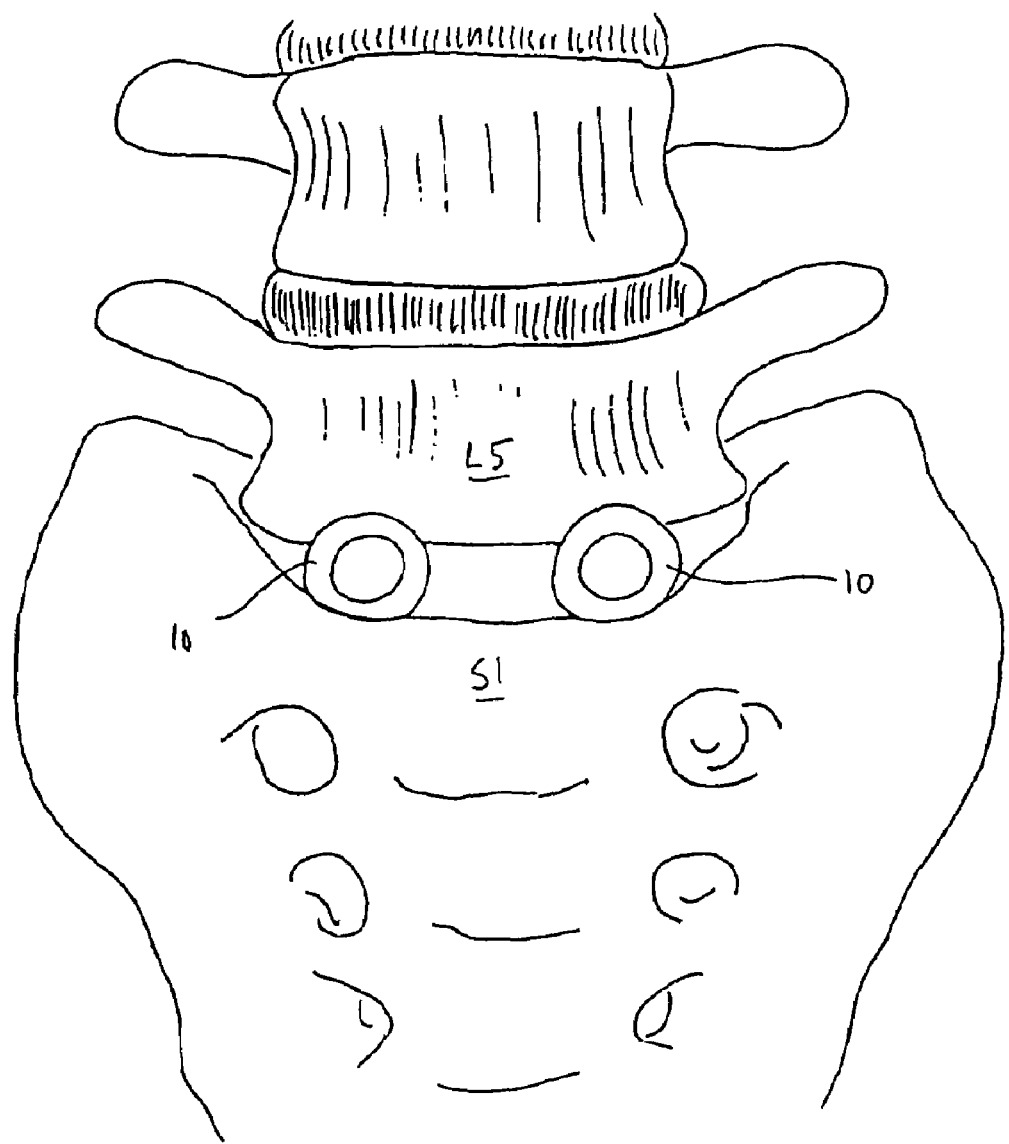
FIG. 2 is a front view of the anterior portion of the lumbosacral region of a human spine, into which a pair of interbody fusion devices of the type shown in FIG. 1 have been implanted.
Figure 3A:
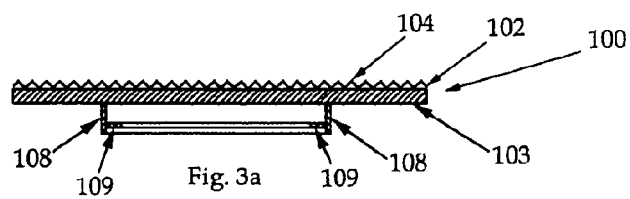
FIGS. 3a and 3b are side cross-section views of the upper and lower opposing plates of the preferred embodiment of the present invention.
Figure 3B:
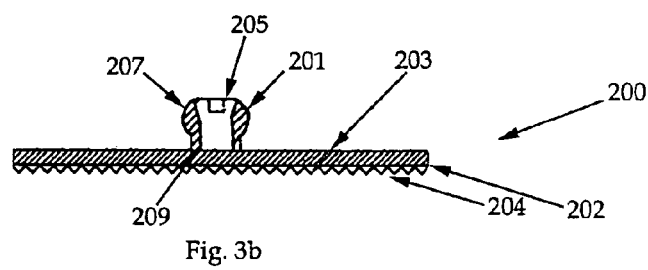

Referring now to FIGS. 3a and 3b, side cross-section views of upper and lower plate members 100,200 of the preferred embodiment of the present invention are shown. As the device is designed to be positioned between the facing surfaces of adjacent vertebral bodies, the plates include substantially flat external face portions 102,202 which seat against the opposing bone surfaces. In addition, the plates are to mate with the bone surfaces in such a way as to not rotate relative thereto. It is, therefore, preferred that the external faces of the plates include a porous coating 104,204 into which the bone of the vertebral body can grow. (Note that this limited fusion of the bone to the base plate does not extend across the intervertebral space.) A hole (not shown) can be provided in the upper plate such that the interior of the device may be readily accessed if a need should arise.

The upper plate 100 includes an internal face 103 that includes an annular retaining wall 108 and an annular retaining ring 109. The lower plate 200 includes an internal face 203 that includes a central post member 201 which rises out of the internal face 203 at a nearly perpendicular angle. The top of this post member 201 includes a ball-shaped head 207. The head 207 includes a series of slots which render it compressible and expandable in correspondence with a radial pressure (or a radial component of a pressure applied thereto). The head 207 includes a central threaded axial bore 209 which extends down the post 201. This threaded bore 209 is designed to receive a set screw 205. Prior to the insertion of the set screw 205, the ball-shaped head 207 of the post 201 can deflect radially inward because of the slots (so that the ball-shaped head contracts). The insertion of the set screw 205 eliminates the capacity for this deflection.

Figure 4A:
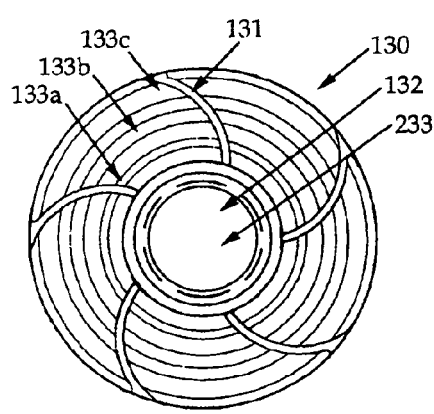
FIGS. 4a and 4b are top and side cross-section view of a belleville washer having radially uniformly spaced concentric grooves of uniform width and depth and spiral slots, for use in a preferred embodiment of the present invention.
Figure 4B:
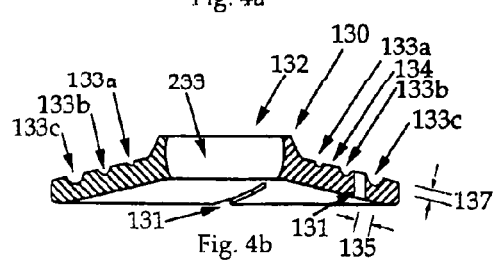

Referring now to FIGS. 4a and 4b, a spirally slotted belleville washer 130 having radially spaced concentric grooves is provided in top and side cross-section views. The belleville washer 130 is a restoring force providing device which comprises a circular shape, having a central opening 132, and which is radially arched in shape. The belleville washer 130 has a radial convexity 134 (i.e., the height of the washer 130 is not linearly related to the radial distance, but may, for example, be parabolic in shape). The restoring force of the belleville washer 130 is proportional to the elastic properties of the material.

The belleville washer 130 comprises a series of spiral slots 131 formed therein. The slots 131 extend from the outer edge of the belleville washer, inward along arcs generally directed toward the center of the element. The slots 131 do not extend fully to the center of the element. In preferred embodiments, the slots may extend anywhere from a quarter to three quarters of the overall radius of the washer, depending upon the requirements of the patient, and the anatomical requirements of the device.

The belleville washer 130 further comprises a series of grooves 133 formed therein. The grooves 133 are concentric and radially spaced from the outer edge of the belleville washer toward the center of the element. In the preferred embodiment shown in FIGS. 4a and 4b, the width 135 of each groove 133 is uniform along the length of the groove 133. Further in the preferred embodiment, the depth 137 of each groove 133 is uniform along the length of the groove 133. Further in the preferred embodiment, each groove 133 has a different width configuration and a different depth configuration than each other groove 133. More specifically, in the preferred embodiment, the width dimension and the depth dimension both vary from groove to groove, each increasing incrementally from groove to adjacent groove with increasing distance from the center of the washer 130. Stated alternatively, grooves that are relatively more narrow and more shallow than the other grooves are closer to the center of the washer, whereas grooves that are relatively wider and deeper than the other grooves are closer to the outer edge of the washer. This is illustrated by example in FIGS. 4a and 4b, which show three concentric grooves 133a-c, with the outermost groove 133c being deeper and wider than groove 133b, which is in turn deeper and wider than groove 133a. Further in the preferred embodiment, the radial spacing of the grooves is uniform.

Figure 5A:
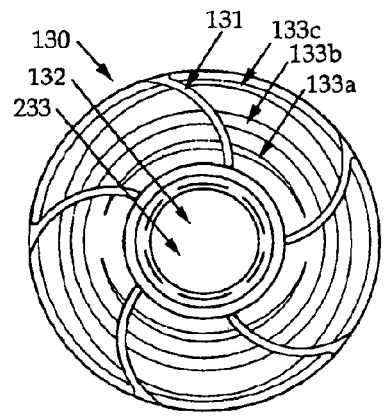
FIGS. 5a-5c are top and side cross-section views of a belleville washer having radially non-uniformly spaced concentric grooves of varying width and depth and spiral slots, for use in an alternate embodiment of the present invention.
Figure 5C:
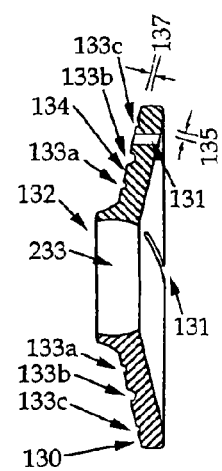
Figure 5B:
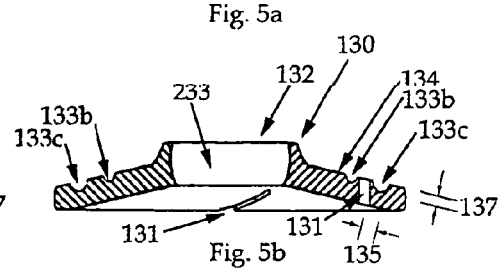

It should be understood that in other embodiments, one or both of the depth and the width of each groove can be (1) increasing along the length of the groove, (2) decreasing along the length of the groove, or (3) varied along the length of each groove, either randomly or according to a pattern. Moreover, in other embodiments, it can be the case that each groove is not formed similarly to one or more other grooves, with or without respect to width and depth dimensions, but rather one or more grooves are formed in any of the above-mentioned fashions, while one or more other grooves are formed in another of the above-mentioned fashions or other fashions. Also, in other embodiments, it can be the case that the radial distance between the grooves is not the same, but rather the spacing increases the closer the space is to the outer edge of the washer, decreases the closer the space is to the outer edge of the washer, or varies either randomly or according to a pattern. Also, while the grooves of the preferred embodiment and the illustrated alternate embodiment have lengths that form closed loops, it should be noted that in other embodiments, the concentric grooves can have lengths that form open loops or arcs; for example, a two concentric grooves forming open loops or arcs can be used in place of a single concentric groove forming a closed loop. It should be clear that any concentric groove pattern can be implemented without departing from the scope of the present invention. To illustrate an alternate embodiment showing an alternate radially spaced concentric groove pattern, FIGS. 5a-5c show a belleville washer 130 having radially spaced concentric grooves 133 in top and side cross-section views, with each groove 133 having a width and a depth each varying along the length of the groove 133, with each groove 133 being formed differently than at least one other groove 133, with the radial spacing of the grooves 133 being varied, and with both closed loops and open loops or arcs being used. In this alternate embodiment, the difference between the grooves 133 is characterized in that the wider and deeper portion of any particular groove 133 is on a different side of the washer 130 than the wider and deeper portion of at least one other groove 133.

As a compressive load is applied to the belleville washer 130 of the present invention, the forces are directed into a hoop stress which tends to radially expand the washer. This hoop stress is counterbalanced by the material strength of the washer, and the force necessary to widen the spiral slots 131 and the radially spaced concentric grooves 133 along with the strain of the material causes a deflection in the height of the washer. Stated equivalently, the belleville washer 130 responds to a compressive load by deflecting compressively; the spiral slots and/or radially spaced concentric grooves cause the washer to further respond to the load by spreading as the slots and/or the grooves in the washer expand under the load. The spring, therefore, provides a restoring force which is proportional to the elastic modulus of the material in a hoop stressed condition.

More particularly, the central opening 132 of the belleville washer is enlarged. This central opening 132 includes a curvate volume 233 for receiving therein the ball-shaped head 207 of the post 201 of the lower plate 200 described above. More particularly, the curvate volume 233 has a substantially constant radius of curvature which is also substantially equivalent to the radius of the ball-shaped head 207 of the post 201. In this embodiment, the spiral slots 131 do not extend all the way to the central opening 132, and approach the opening only as far as the material strength of the washer can handle without plastically deforming under the expected anatomical loading. Preferably, the center of the washer is flat; therefore, the central opening 132 can be formed from flat edges. It should be understood that this is not required, but rather is preferred.

Figure 6A:
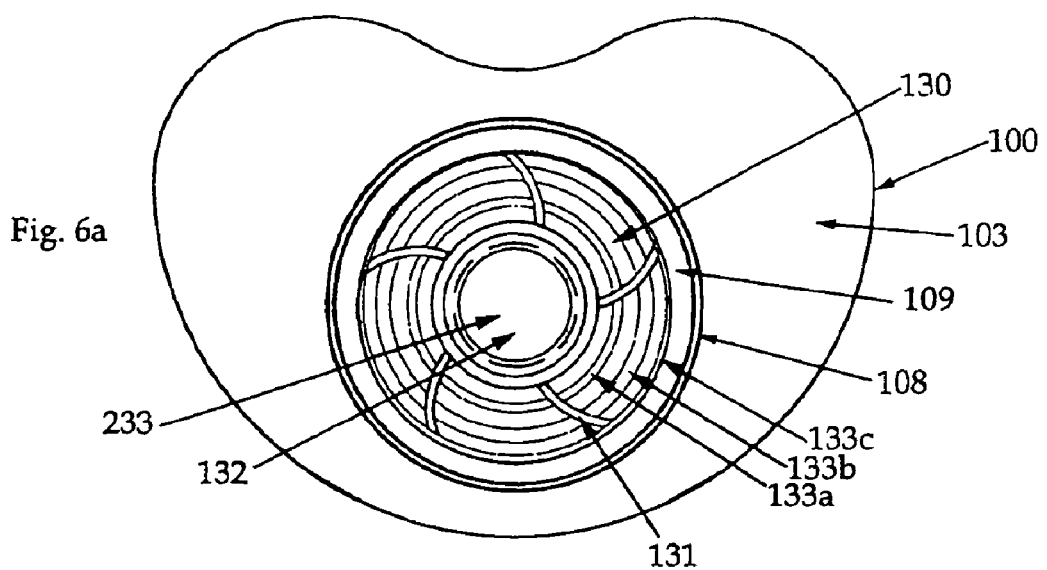
FIG. 6a is a top view of the upper plate of FIG. 3a, with the belleville washer of FIGS. 4a and 4b fitted within a retaining wall and a retaining ring of the upper plate.
Figure 6B:
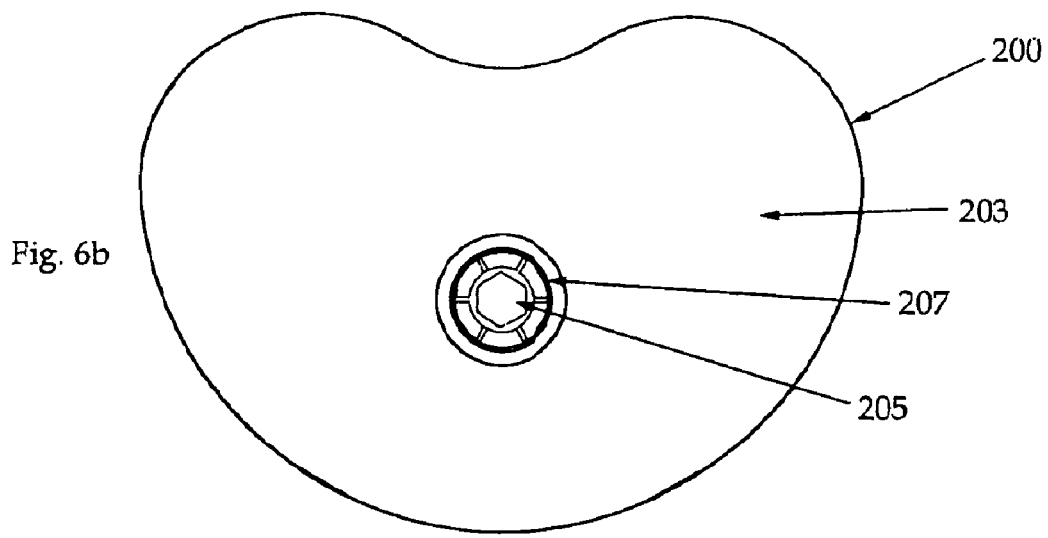
FIG. 6b is a top view of the lower plate of FIG. 3b.

Referring now to FIG. 6a, a top view of the upper plate 100 of FIG. 3a, with the spirally slotted and concentrically grooved belleville washer 130 of FIGS. 4a and 4b fitted within a retaining wall 108 and a retaining ring 109 of the upper plate 100, is shown. The diameter of the retaining wall 108 is preferably slightly wider than the diameter of the undeflected belleville washer 130 such that the loading thereof can result in an unrestrained radial deflection of the washer 130. FIG. 6b shows a top view of the lower plate 200 of FIG. 3b.

Figure 7:
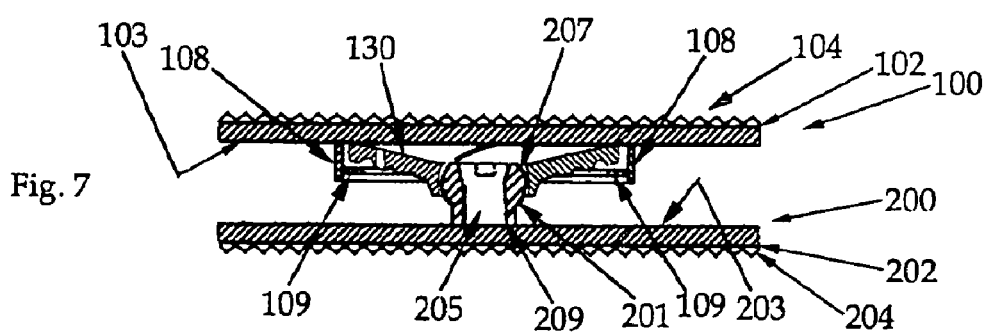
FIG. 7 is a side cross-section view of the preferred embodiment of the present invention, which utilizes a belleville washer of the type shown in FIGS. 4a and 4b, showing the plates of FIGS. 6a and 6b assembled together.

FIG. 7 shows the fully assembled preferred embodiment of the present invention. The spirally slotted and radially grooved belleville washer 130 of FIGS. 4a and 4b is placed with its wide end against the top plate 100 within the annular retaining wall 108 as shown in FIG. 6b. The annular retaining ring 109 is provided to hold the belleville washer 130 against the internal face 103 of the upper plate 100 within the retaining wall 108. The post 201 of the lower plate 200 is fitted into the central opening 132 of the belleville washer 130 (the deflectability of the ball-shaped head 207 of the post 201, prior to the insertion of the set screw 205, permits the head 207 to be inserted into the interior volume 233 at the center of the belleville washer 130. Subsequent introduction of the set screw 205 into the axial bore 209 of the post 201 eliminates the deflectability of the head 207 so that the washer 130 cannot be readily removed therefrom, but can still rotate thereon. In some embodiments (not in this preferred embodiment), the post head 207 can be locked tightly within the central volume 233 of the belleville washer 130 by the tightening of the set screw 205, to prevent any rotation of the plates 100,200. Compressive loading of the assembly causes the washer 130 to deflect (with the spiral slots and the radially spaced concentric grooves enhancing the deflection) so that the wide end radially expands while being maintained centrally against the upper plate 100 by the retaining wall 108 and the retaining ring 109. When the load is removed, the washer 130 springs back to its original shape.

Figure 8A:
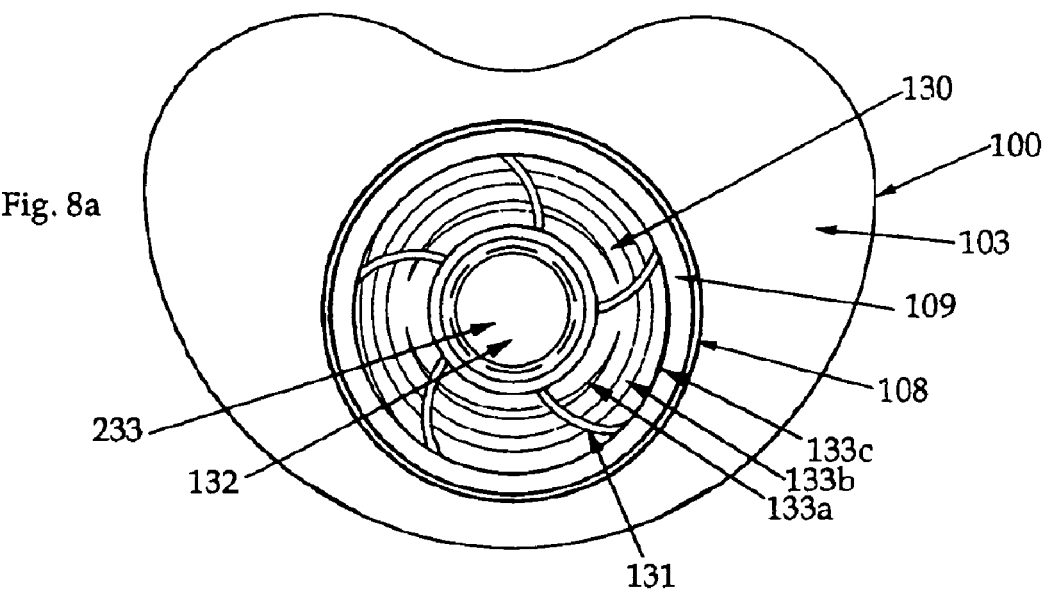
FIG. 8a is a top view of the upper plate of FIG. 3a, with the belleville washer of FIGS. 5a-5c fitted within a retaining wall and a retaining ring of the upper plate.
Figure 8B:
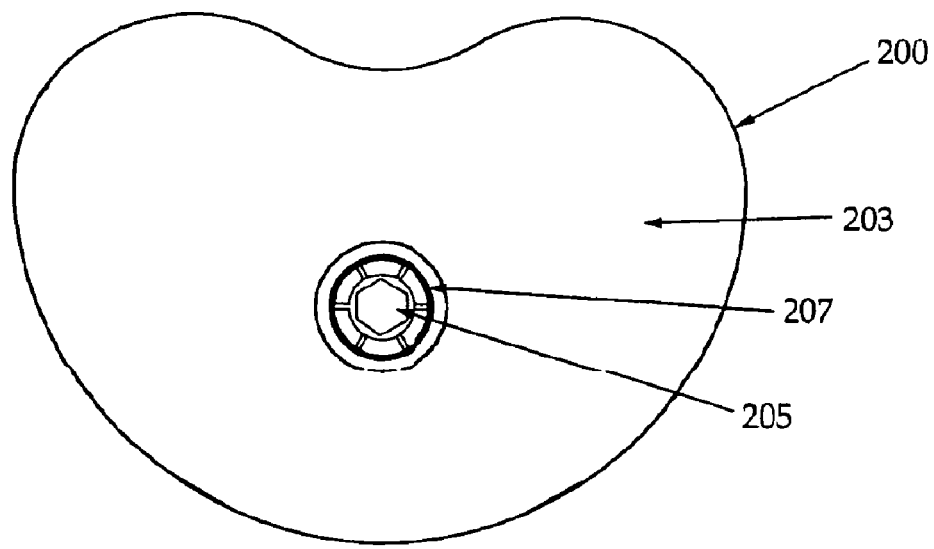
FIG. 8b is a top view of the lower plate of FIG. 3b.

Referring now to FIG. 8a, a top view of the upper plate 100 of FIG. 3a, with the spirally slotted and concentrically grooved belleville washer 130 of FIGS. 5a-5c fitted within a retaining wall 108 and a retaining ring 109 of the upper plate 100, is shown. The diameter of the retaining wall 108 is preferably slightly wider than the diameter of the undeflected belleville washer 130 such that the loading thereof can result in an unrestrained radial deflection of the washer 130. FIG. 8b shows a top view of the lower plate 200 of FIG. 3b.

Figure 9:
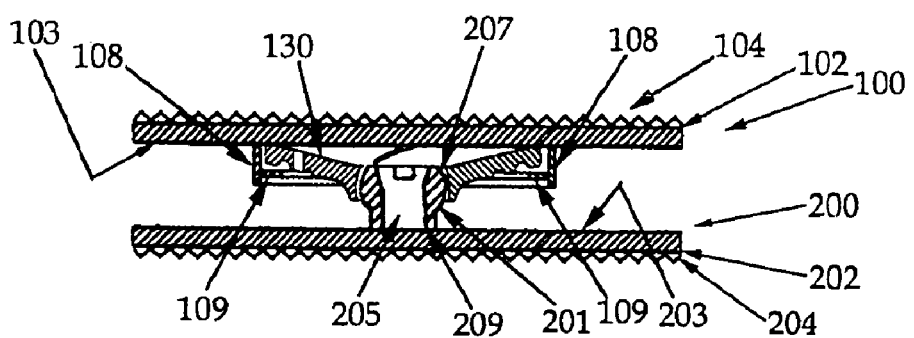
FIG. 9 is a cross-section view of an alternate embodiment of the present invention, which utilizes a belleville washer of the type shown in FIGS. 5a-5c, showing the plates of FIGS. 8a and 8b assembled together.

FIG. 9 shows a fully assembled alternate embodiment of the present invention. The spirally slotted and concentrically grooved belleville washer 130 of FIGS. 5a-5c is placed with its wide end against the top plate 100 within the annular retaining wall 108 as shown in FIG. 6b. The annular retaining ring 109 is provided to hold the belleville washer 130 against the internal face 103 of the upper plate 100 within the retaining wall 108. The post 201 of the lower plate 200 is fitted into the central opening 132 of the belleville washer 130 (the deflectability of the ball-shaped head 207 of the post 201, prior to the insertion of the set screw 205, permits the head 207 to be inserted into the interior volume 233 at the center of the belleville washer 130, and the washer 130 to be rotated into the desired angulation; subsequent introduction of the set screw 205 into the axial bore 209 of the post 201 eliminates the deflectability of the head 207 so that the washer 130 cannot be readily removed therefrom, but can still rotate thereon.). The post head 207 can be locked tightly within the central volume 233 of the belleville washer 130 by the tightening of the set screw 205, to prevent any rotation of the plates 100,200. Compressive loading of the assembly causes the washer 130 to deflect (with the spiral slots and radially spaced concentric grooves enhancing the deflection) so that the wide end radially expands while being maintained centrally against the upper plate 100 by the retaining wall 108 and the retaining ring 109. When the load is removed, the washer 130 springs back to its original shape.

Inasmuch as the human body has a tendency to produce fibrous tissues in perceived voids, such as may be found within the interior of the present invention, and such fibrous tissues may interfere with the stable and/or predicted functioning of the device, some embodiments of the present invention (although not the preferred embodiment) will be filled with a highly resilient and biologically inert elastomeric material. Suitable materials may include hydrophilic monomers such as are used in contact lenses. Alternative materials include silicone jellies and collagens such as have been used in cosmetic applications.

While there has been described and illustrated specific embodiments of an intervertebral spacer device, it will be apparent to those skilled in the art that variations and modifications are possible without deviating from the broad spirit and principle of the present invention. The invention, therefore, shall not be limited to the specific embodiments discussed herein.

We claim:

1. An intervertebral spacer device comprising:
   first and second plates, each having inner and outer surfaces thereof, said plates being disposed in a spaced apart relationship such that the inner surfaces face toward one another, and the outer surfaces face away from one another, said first plate including a retaining wall extending outwardly from said inner surface of said first plate; and
at least one belleville washer, having narrow and wide ends thereof, disposed with said wide end contacting said inner surface of said first plate within said retaining wall, such that a compressive load applied to the outer surfaces of said plates is counteracted by said at least one belleville washer, said at least one belleville washer including at least one radially spaced concentric groove and at least one spiral slot, wherein said at least one radially spaced concentric groove in said at least one belleville washer is at a respective distance from an outer edge of said at least one belleville washer, wherein at least one of either an at least one depth of said at least one radially concentric groove increases incrementally with decreasing said distance, or an at least one width of said at least one radially concentric groove increases incrementally with decreasing said distance,
   wherein said at least one radially spaced concentric groove in said belleville washer comprises a plurality of radially spaced concentric grooves, and wherein each of said plurality of radially spaced concentric grooves in said belleville washer has a respective length, a respective depth along said respective length, and respective width along said respective length, at least one of said respective depth and said respective width being uniform along said respective length, wherein said length forms a closed loop.

2. The device as set forth in claim 1, wherein one of said first and second plate members further comprises a post structure extending outwardly from said first surface of said one of said first and second plate members, and which post structure includes a ball-shaped head.

3. The device as set forth in claim 2, wherein said post structure further includes a threaded bore which extends axially from said ball-shaped head toward said first surface of said one of said first and second plate members, and which bore receives therein a threaded set screw such that prior to an insertion of the set screw therein, said bore permits the ball-shaped head to compress radially inwardly, and such that after the insertion of said set screw said ball-shaped head is not readily radially compressible.

4. The device as set forth in claim 3, wherein said at least one belleville washer further comprises a central opening which includes a curvate volume for receiving and holding therein said ball-shaped head.

5. The device as set forth in claim 4, wherein a tightening of said set screw locks said curvate volume with respect to said ball-shaped head.

6. The device as set forth in claim 1, wherein said at least one spiral slot in said belleville washer comprises a plurality of spaced apart spiral slots, each of which extends from a locus on a peripheral edge of said belleville washer to a locus which is radially in from said peripheral edge.

7. The device as set forth in claim 1, wherein the radial spacing of said plurality of radially spaced concentric grooves is non-uniform.

8. An intervertebral spacer device comprising:
   first and second plates, each having inner and outer surfaces thereof, said plates being disposed in a spaced apart relationship such that the inner surfaces face toward one another, and the outer surfaces face away from one another, said first plate including a retaining wall extending outwardly from said inner surface of said first plate; and
at least one belleville washer, having narrow and wide ends thereof, disposed with said wide end contacting said inner surface of said first plate within said retaining wall, such that a compressive load applied to the outer surfaces of said plates is counteracted by said at least one belleville washer, said at least one belleville washer including at least one radially spaced concentric groove and at least one spiral slot,
   wherein said at least one radially spaced concentric groove in said at least one belleville washer is at a respective distance from an outer edge of said at least one belleville washer, wherein at least one of either an at least one depth of said at least one radially concentric groove increases incrementally with decreasing said distance, or an at least one width of said at least one radially concentric groove increases incrementally with decreasing said distance, wherein said at least one radially spaced concentric groove in said belleville washer comprises a plurality of radially spaced concentric grooves, and wherein each of said plurality of radially spaced concentric grooves in said belleville washer has a respective length, a respective depth along said respective length, and a respective width along said respective length, at least one of said respective depth and said respective width being uniform along said respective length, wherein the radial spacing of said plurality of radially spaced concentric grooves is uniform.

9. The device as set forth in claim 8, wherein said length forms an open loop.

10. The device as set forth in claim 8, wherein one of said first and second plate members further comprises a post structure extending outwardly from said first surface of said one of said first and second plate members, and which post structure includes a ball-shaped head.

11. The device as set forth in claim 10, wherein said post structure further includes a threaded bore which extends axially from said ball-shaped head toward said first surface of said one of said first and second plate members, and which bore receives therein a threaded set screw such that prior to an insertion of the set screw therein, said bore permits the ball-shaped head to compress radially inwardly, and such that after the insertion of said set screw said ball-shaped head is not readily radially compressible.

12. The device as set forth in claim 11, wherein said at least one belleville washer further comprises a central opening which includes a curvate volume for receiving and holding therein said ball-shaped head.

13. The device as set forth in claim 12, wherein a tightening of said set screw locks said curvate volume with respect to said ball-shaped head.

14. The device as set forth in claim 8, wherein said at least one spiral slot in said belleville washer comprises a plurality of spaced apart spiral slots, each of which extends from a locus on a peripheral edge of said belleville washer to a locus which is radially in from said peripheral edge.

15. An intervertebral spacer device comprising:
first and second plates, each having inner and outer surfaces thereof, said plates being disposed in a spaced apart relationship such that the inner surfaces face toward one another, and the outer surfaces face away from one another, said first plate including a retaining wall extending outwardly from said inner surface of said first plate; and
at least one belleville washer, having narrow and wide ends thereof, disposed with said wide end contacting said inner surface of said first plate within said retaining wall, such that a compressive load applied to the outer surfaces of said plates is counteracted by said at least one belleville washer, said at least one belleville washer including at least one radially spaced concentric groove and at least one spiral slot, said at least one radially spaced concentric groove in said at least one belleville washer is at a respective distance from an outer edge of said at least one belleville washer, wherein at least one of either an at least one depth of said at least one radially concentric groove increases incrementally with decreasing said distance, or an at least one width of said at least one radially concentric groove increases incrementally with decreasing said distance,
wherein said at least one radially spaced concentric groove in said belleville washer comprises a plurality of radially spaced concentric grooves, and wherein each of said plurality of radially spaced concentric grooves in said at least one belleville washer has a respective length, a respective depth along said respective length, and a respective width along said respective length, and wherein at least one of said depths is different than at least one other of said depths, and wherein at least one of said widths is different than at least one other of said widths.

16. The device as set forth in claim 15, wherein said at least one radially spaced concentric groove in said belleville washer comprises a plurality of radially spaced concentric grooves, and wherein each of said plurality of radially spaced concentric grooves in said belleville washer has a respective length, a respective depth along said respective length, and a respective width along said respective length, at least one of said respective depth and said respective width being uniform along said respective length.

17. The device as set forth in claim 16, wherein said length forms an open loop.

18. The device as set forth in claim 16, wherein the radial spacing of said plurality of radially spaced concentric grooves is non-uniform.

19. The device as set forth in claim 15, wherein one of said first and second plate members further comprises a post structure extending outwardly from said first surface of said one of said first and second plate members, and which post structure includes a ball-shaped head.

20. The device as set forth in claim 19, wherein said post structure further includes a threaded bore which extends axially from said ball-shaped head toward said first surface of said one of said first and second plate members, and which bore receives therein a threaded set screw such that prior to an insertion of the set screw therein, said bore permits the ball-shaped head to compress radially inwardly, and such that after the insertion of said set screw said ball-shaped head is not readily radially compressible.

21. The device as set forth in claim 20, wherein said at least one belleville washer further comprises a central opening which includes a curvate volume for receiving and holding therein said ball-shaped head.

22. The device as set forth in claim 21, wherein a tightening of said set screw locks said curvate volume with respect to said ball-shaped head.

23. The device as set forth in claim 15, wherein said at least one spiral slot in said belleville washer comprise a plurality of spaced apart spiral slots, each of which extends from a locus on a peripheral edge of said belleville washer to a locus which is radially in from said peripheral edge.

* * * * *

UNITED STATES PATENT AND TRADEMARK OFFICE
CERTIFICATE OF CORRECTION

| | | |
|---|---|---|
| PATENT NO. | : 7,713,302 B2 | |
| APPLICATION NO. | : 10/833737 | |
| DATED | : May 11, 2010 | |
| INVENTOR(S) | : James D. Ralph et al. | |

It is certified that error appears in the above-identified patent and that said Letters Patent is hereby corrected as shown below:

Col. 1, Line 23, after "by" insert --referenced herein in their respective entireties--

Col. 10, Line 17, after "and" insert --a--

Signed and Sealed this
Fourteenth Day of June, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,713,302 B2 | Page 1 of 1 |
| APPLICATION NO. | : 10/833737 | |
| DATED | : May 11, 2010 | |
| INVENTOR(S) | : James D. Ralph et al. | |

It is certified that error appears in the above-identified patent and that said Letters Patent is hereby corrected as shown below:

In the Specification
Col. 1, Line 22, before "of" insert --All--
Col. 1, Line 23, after "by" insert --referenced herein in their respective entireties--
Col. 1, Line 55, "spine" should read --"spine"--

In the Claims
Col. 10, Line 17, after "and" insert --a--

This certificate supersedes the Certificate of Correction issued June 14, 2011.

Signed and Sealed this
Eighteenth Day of February, 2014

Michelle K. Lee
*Deputy Director of the United States Patent and Trademark Office*